(12) United States Patent
Hafner

(10) Patent No.: US 7,799,027 B2
(45) Date of Patent: *Sep. 21, 2010

(54) ELECTROSURGICAL INSTRUMENT

(75) Inventor: Dieter Hafner, Tubingen (DE)

(73) Assignee: ERBE Elektromedizin GmbH, Tübingen (DE)

(*) Notice: Subject to any disclaimer, the term of this patent is extended or adjusted under 35 U.S.C. 154(b) by 755 days.

This patent is subject to a terminal disclaimer.

(21) Appl. No.: 11/573,287

(22) PCT Filed: Jul. 15, 2005

(86) PCT No.: PCT/EP2005/007737
§ 371 (c)(1),
(2), (4) Date: Feb. 6, 2007

(87) PCT Pub. No.: WO2006/018086
PCT Pub. Date: Feb. 23, 2006

(65) Prior Publication Data
US 2008/0071268 A1 Mar. 20, 2008

(30) Foreign Application Priority Data
Aug. 11, 2004 (DE) ......................... 10 2004 039 053
Nov. 18, 2004 (DE) ......................... 10 2004 055 669

(51) Int. Cl.
*A61B 18/18* (2006.01)
(52) U.S. Cl. .......................................... 606/51; 606/171
(58) Field of Classification Search ............. 606/48–52, 606/171; 607/101
See application file for complete search history.

(56) References Cited
U.S. PATENT DOCUMENTS
5,443,463 A 8/1995 Stern et al.

(Continued)

FOREIGN PATENT DOCUMENTS
WO 9717033 5/1997

*Primary Examiner*—Linda C Dvorak
*Assistant Examiner*—Benjamin Lee
(74) *Attorney, Agent, or Firm*—Dickstein Shapiro LLP

(57) ABSTRACT

The invention relates to an electrosurgical instrument comprising two limbs that have an articulated connection and that can be actuated in the manner of a cutting or a clamping tool. The instrument also comprises opposing electrode parts with coagulation surfaces on distal ends of its limbs for holding a vessel or tissue and for passing a current through said vessel or tissue to cause it to coagulate. At least one electrode part has an open region that acts as a guide gap for a cutting instrument, so that the electrode part(s) is/are divided into at least two areas and the cutting instrument can be applied to the clamped vessel or tissue to execute a cutting operation. In addition, current supply devices supply the coagulation current from a high-frequency generator to the electrode parts. The improved configuration of said electrosurgical instrument allows the open region on the electrode part(s) to afford optimal guidance of a cutting instrument, whereby said open region can be easily prepared for additional cutting operations and/ or be subjected to an after-treatment. To achieve this, the two or more open regions of the electrode part(s) comprise respective opposing separation surfaces that taper in the direction of the coagulation surfaces.

18 Claims, 3 Drawing Sheets

U.S. PATENT DOCUMENTS

| | | |
|---|---|---|
| 5,797,938 A | 8/1998 | Paraschac et al. |
| 5,891,142 A | 4/1999 | Eggers et al. |
| 5,944,718 A | 8/1999 | Austin et al. |
| 6,273,887 B1 | 8/2001 | Yamauchi et al. |
| 6,775,575 B2 * | 8/2004 | Bommannan et al. ....... 607/101 |
| 2003/0171747 A1 * | 9/2003 | Kanehira et al. .............. 606/45 |
| 2003/0181910 A1 * | 9/2003 | Dycus et al. .................. 606/51 |
| 2003/0229344 A1 | 12/2003 | Dycus et al. |
| 2004/0049185 A1 | 3/2004 | Latterell et al. |
| 2004/0116979 A1 | 6/2004 | Truckai et al. |

* cited by examiner

ELECTROSURGICAL INSTRUMENT

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The invention relates to an electrosurgical instrument comprising two limbs that have an articulated connection and that can be actuated in the manner of a cutting or clamping tool.

BACKGROUND OF THE INVENTION

Electrosurgical instruments have been used for many years in high-frequency surgery especially in order to coagulate biological tissue as well as to cut it. For coagulation a high-frequency current is passed through the tissue to be treated, so that it changes due to protein coagulation and dehydration. The tissue contracts in such a way that the vessels are closed and bleeding is staunched. After coagulation has taken effect the tissue can, for example, be separated by means of a mechanically operating cutting instrument.

Electrosurgical procedures can be carried out in a monopolar as well as a bipolar way. With monopolar technology the electrosurgical instrument has only one current supply and the tissue to be treated (or the patient) must therefore be placed at the other potential. Bipolar instruments which are constructed with two separately isolated sections are gaining more and more in significance, however. The current path between the electrode parts can thus be calculated and does not run long distances through the body of the patient. The effect of, for example, pacemakers or other equipment which are connected to the patient during an operation is thus reduced.

Bipolar coagulation instruments comprise essentially two limbs that have an articulated connection at whose proximal ends handle devices are provided for handling the limbs. At the distal ends of the limbs are electrode parts with coagulation surfaces for gripping the tissue and for passing the coagulation current through the tissue. For this the HF current supplied by a HF generator is fed via current supply devices to the electrode parts of the bipolar instrument.

Known bipolar coagulation instruments often comprise open regions on the electrode parts forming a guide gap for a cutting instrument. This means that the electrode parts are at least partially divided, so that cutting instrument can be placed on the tissue clamped between the electrode parts. The guide gap therefore facilitates access for the cutting instrument to the tissue while being held between the electrode parts of the coagulation instrument. Also, the guide gap is provided to guide the cutting instrument in order to guarantee precise cutting of the tissue. This is advantageous particularly for mechanically operated cutting instruments.

Such an instrument is, for example, known from US 2003/0229344 A1. Bipolar tongs are shown where the effector unit and in particular its electrically conductive areas comprise slits to facilitate access for a cutting instrument to the tissue clamped in the effector unit. The slits are constructed in such a way that the coagulation surfaces of the electrode parts are disrupted as little as possible. With this embodiment of the slits their preparation for reuse, that is to say cleaning, is very time-consuming as the access into the slits is made difficult.

In order to counteract this problem a very wide slit or guide gap is provided in other known instruments. Here a considerable reduction in the coagulation surfaces or insufficient guidance of mechanical cutting instruments in particular has to be accepted.

Known instruments are also provided as disposable instruments in order to save cleaning. This has considerable cost implications.

BRIEF SUMMARY OF THE INVENTION

The object of the invention is to provide an electrosurgical instrument for coagulation of tissue wherein an open region is permanently available on least at one electrode part for optimum guidance of a cutting instrument.

According to the invention there is provided an electrosurgical instrument which includes two limbs that have an articulated connection which can be actuated corresponding to a cutting or a clamping tool. The instrument further includes electrode parts positioned opposite each other with coagulation surfaces at distal ends of the limbs for gripping a vessel or tissue and for passing a coagulation current through the vessel or tissue for its coagulation. At least one electrode part comprises an open region as a guide gap for a cutting instrument, so that at least one electrode part is divided into two areas and the cutting instrument can be applied to the vessel or tissue held in order to carry out a cutting procedure. Moreover, current supply devices are provided for passing the coagulation current from a HF generator to the electrode parts. The at least two areas of the at least one electrode part comprise respective separation surfaces arranged opposite each other and taper in the direction of the coagulation surfaces.

The basis of the invention is that the guide gap expands in the direction which faces away from a cutting area between the electrode parts on both electrode parts. Precise guidance of the cutting instrument is thus possible in direct proximity to the cutting area based on the tapered construction of the guide gap. The coagulation zone of the electrode parts is hardly disrupted. The other areas of the guide gap are at the same time easily accessible and thus easy to clean. If the guide gap has to be re-worked, for example a coating having to be applied, then this can be carried out easily because of the improved access.

In a preferred first embodiment the open regions are provided at the opposite electrode parts wherein these are essentially aligned when the limbs are brought together. If only one open region has been formed at one electrode part this is especially suitable for cutting tissue with, for example, a surgical knife, wherein the tissue rests completely on the opposite electrode part in a tensioned state. If open regions are provided at both electrode parts surgical scissors can, for example, be used on the coagulated tissue and this is easily cut. In order that a well-calculated cut can be carried out the open regions are preferably arranged in the central sections of the electrode parts.

In a further preferred embodiment the cutting instrument is combined with the electrosurgical instrument. The cutting instrument is, for example, situated within one of the limbs and can be brought into a cutting position when required. A change of instruments is thus avoidable, so that the course of an operation does not have to be disrupted.

With the cutting instrument integrated in the coagulation instrument both electrode parts are preferably constructed with the open region, so that the cutting instrument can reach the tissue unhindered.

If the cutting instrument is not constructed so that it is integrated with the electrosurgical instrument, the guide gap has then to be arranged in such a way that a cutting instrument introduced from the outside can be placed with sufficient accuracy at the pretensioned tissue.

One advantageous embodiment provides for the cutting instrument being mechanically and/or electrically operated. A blade constructed on a shaft on the electrosurgical instrument can, for example, be provided which is housed in the limb during coagulation and is applied to the tissue for the cutting procedure. Positioning of the blade or another cutting instrument and also feeding it forward can occur automatically or be carried out by the surgeon mechanically.

A solution according to the invention provides for the cutting instrument being constructed for cutting by means of a HF-current and for being connected to a control unit, so that the cutting current supply depends on the operation phases. The surgeon can control the cutting procedure so that it runs automatically and is optimised.

In a preferred embodiment it is provided that the electrode parts comprise at least one tensioning area each in such a way that when clamping the tissue it is pretensioned between the electrode parts and the cutting procedure can be carried out on the pretensioned tissue by means of the cutting instrument. The tissue under tension is then easier to cut by means of the cutting instrument in particular by means of a mechanical cutting instrument, as tissue fibres are aligned at right angles to the cutting direction and the tissue becomes thinner in the procedure. The force needed to completely cut pretensioned tissue is thus considerably reduced and mechanical stress on the cutting instrument, in particular wear of cutting sections, is counteracted. The cutting procedure itself is also easier for the surgeon and the instrument is easier to handle. As a result of the separation surfaces of the electrode parts tapering towards the cutting area a mechanically operated cutting instrument in particular can be applied easily at the guide gap.

In a preferred embodiment one of the tensioning areas has a convex curvature at least in a first central section while the tensioning area positioned opposite has a concave curvature at least have essentially a positive fit. As a result of the curved tensioning areas tensioning of the tissue is facilitated in the simplest way because it is pulled, that is to say stretched, by the curved areas on both sides in the direction of their end areas. Because of the tight fit the tissue tensioned between the limbs is securely held in a tensioned state.

The terms "convex" and "concave" in this context are not just to be understood as meaning a rounded arc. Rather, these terms both here and in the claims are intended to cover not only a surface which defines a rounded arc but also any kind of elevation or recess, hence also a roof-like elevation and thus a V-shaped recess.

In a further preferred embodiment one of the tensioning areas has a convex curvature at least in a first central section while the tensioning area positioned opposite has a concave curvature at least in the second central section. A radius of curvature of the concave tensioning area at least in the second central section is greater than a radius of curvature of the convex tensioning area in the first central section. The curvatures run along the longitudinal axes of the distal ends in such a way that the vessel or tissue that is held between the distal ends and extends perpendicularly to the longitudinal axes is held with a pressure that increases towards the first and second central sections. Based on the different curvatures of the coagulation surfaces contact between the coagulation surfaces can, seen mathematically, only occur at their crests. This means that an area of maximal proximity is formed between the coagulation surfaces that extends symmetrically around the crests of the coagulation surfaces. In this area tissue is particularly strongly pressed together as a result of the limbs being brought together due to the increased pressure compared to the other coagulation areas and is thus safely held between the electrode parts.

It is advantageous that the smooth geometry is easy to produce, inhibits adherence of tissue during the procedure and the coagulation surfaces can be easily prepared for reuse and if required reconditioned. In addition secure closure of a vessel or tissue is achieved as a result of the high clamping force in the area of high pressure.

In one of the solutions according to the invention it is provided that at one tensioning area and/or on the opposite tensioning area a surface profile is formed which supports the tensioning effect. The profile is preferably formed at the end areas of the respective tensionings and moves the tissue additionally in a direction of pull defined by the tensioning areas or prevents a backward movement of the tissue against this direction of pull.

The surface profile supporting the tensioning effect is preferably constructed as a saw tooth profile. The teeth of the profile can, for example, be arranged in such a way that during the bringing together of the limbs they increasingly grip the tissue and transport it in the direction of pull. This increases the tension in the tissue considerably. Care must, however, be taken that injury to the tissue caused by the profile is avoided, so that the teeth are preferably constructed as rounded-off nodules.

The profile is preferably constructed in such a way that the tissue is held by the profile in its tensioned position when the limbs are slightly opened. The profile acts therefore as an arrangement of barbs.

In a preferred embodiment the surface profile supporting the tensioning effect is constructed in such a way that at least one constriction is provided between the electrode parts. This is particularly efficient with electrode parts which have the same radii of curvature. This means that the coagulation surfaces of the electrode parts, constructed in particular with the same radius of curvature, are preferably constructed at both end areas in such a way that while bringing the limbs together the tissue is transported in the direction of the end areas and is clamped in a respective constriction opposite the remaining area when the limbs have been brought together. This constriction has the additional advantage that the coagulation surfaces can essentially have a smooth construction and are thus easy to clean. Injury to the tissue is also avoided on account of the smooth surface.

In an advantageous embodiment an insulating section is formed on at least one of the coagulation surfaces, so that direct electrical contact between the coagulation surfaces can be prevented. Due to the heat conducting properties of the insulating section coagulation of the tissue is also guaranteed at this section. The insulating section depending on the construction of the electrode parts is to be provided at the areas of at least one coagulation surface which are closest to the opposite coagulation surface. This has to be taken into consideration in particular when the tensioning areas and thus the coagulation surfaces have a different radius of curvature. The insulating section is then preferably arranged at the central section of the tensioning area or tensioning areas, thus preventing a short circuit between the electrode parts. The tensioning effect is further enhanced simultaneously by the insulating section.

If the insulating section is constructed at the areas of at least one coagulation surface in closest proximity to the opposite coagulation surface it can close flush with the respective coagulation surface. The surface part of the coagulation surface which describes the area in closest proximity to the opposite coagulation surface must then be constructed from continuous insulating material, so that contact between the conductive areas of the coagulation surfaces is prevented. With convex or concave tensioning areas positioned opposite or coagulation surfaces having different radii of curvature the insulating section would have to be arranged along one crest of at least one coagulation surface. It is advantageous that the insulating section in this embodiment is protected by being housed in the respective electrode part and is thus safe from wear.

Alternatively, it is possible to construct the insulating surface in such a way that it protrudes from the respective coagulation surface. In this case the insulating section does not just serve the purpose of insulating, but also to bend the tissue to be treated several times in order to achieve better holding of the tissue between the distal ends of the electrosurgical instrument.

In a preferred embodiment the insulating section, that is to say the insulating section protruding from the respective coagulation surface, is constructed from several part sections. This facilitates an especially secure hold of the tissue between the electrode parts because the tissue is bent several times at the edges of the insulating section.

One solution according to the invention provides for constructing the insulating section itself to be structured in order to achieve an optimal hold of the tissue.

A preferred embodiment provides for the insulating section being constructed from ceramic or diamond. Advantageously both ceramic and diamond comprise amongst other things a high corrosion resistance and high wear resistance to mechanical stress.

In a further preferred embodiment the insulating section is formed as the particular or each surface profile supporting the particular or each tensioning effect. A short circuit is thus prevented from occurring between the electrode parts in the simplest way as well as the tensioning of the tissue being increased.

A device preventing a short circuit between the electrode parts can, for example, also be provided at the limbs. If, for example, a spacer has been arranged thereon, the limbs cannot be brought together completely and a gap remains between the electrode parts.

Electrosurgical instruments of this kind can, for example, be constructed for use on an open body cavity. The principle of the electrode parts having a tensioning area can, however, also be employed for instruments used in endoscopies. The electrode parts attached to the limbs and if required the cutting instrument are then, for example, operated via a handle attached to a shaft or a control unit is provided, so that actuation of the electrode parts and/or the cutting instrument is controlled by the same. The electrosurgical instrument is thus preferably constructed as a laparoscopic instrument.

Embodiment of the invention will now be described by way of example with reference to the accompanying drawings.

DETAILED DESCRIPTION OF THE INVENTION

Figure 1:
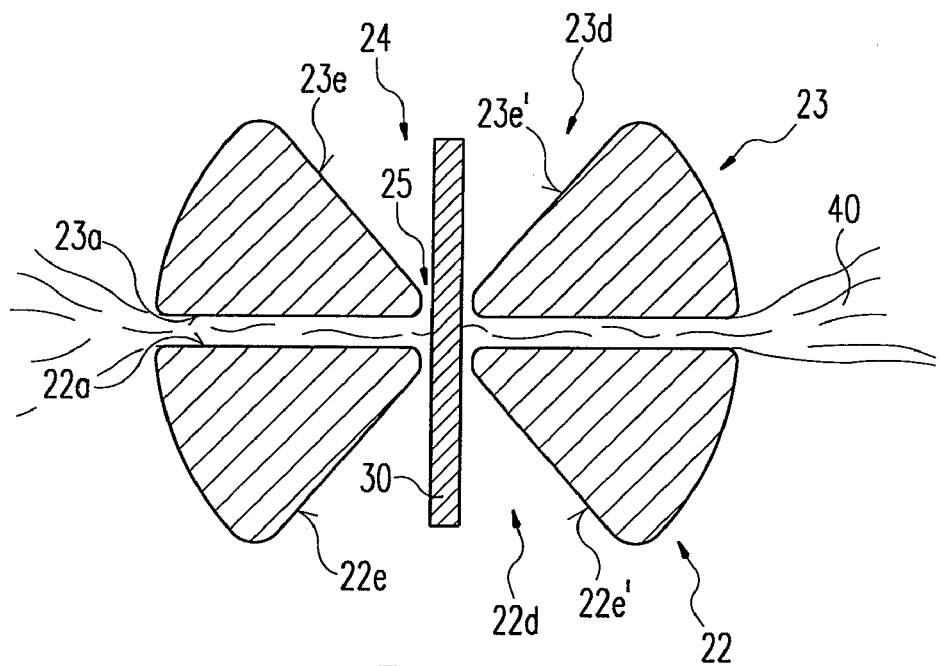
FIG. 1 is a schematic cross-sectional view from the front of an electrode arrangement a first embodiment of electrosurgical instrument.

The same reference numerals will be used in the following description for the same parts and parts with the same function.

FIG. 1 shows a schematic front view section of the enlarged electrode layout according to a first preferred embodiment. The electrode layout is, for example, provided on an electrosurgical instrument, as described in more detail in FIG. 2. The electrode parts 22, 23 comprise open regions 22d, 23d which form a guide gap 24 for a cutting instrument 30. Due to the open regions 22d, 23d the electrode parts 22, 23 comprise two respective areas. The cutting instrument 30 can therefore be placed on the clamped tissue 40 for carrying out a cutting procedure. The guide gap 24 also facilitates a precise cut of the tissue 40, because the cutting instrument 30 can be guided along the guide gap 24. This is advantageous when the cutting instrument 30 is operated mechanically. As can be seen from the diagram the open regions 22d, 23d are aligned so as not to impede the cutting procedure. At least two areas of the respective electrode parts 22, 23 comprise respective separation surfaces 22e, 22e', 23e, 23e' opposite each other tapering in the direction of the coagulation surfaces 22a, 23a. The guide gap 24 thus expands in the direction facing away from a cutting area 25 between the electrode parts 22, 23 at each electrode part 22, 23.

Based on the tapered construction of the guide gap 24 precise guidance of the cutting instrument 30 is possible in the direct proximity of the cutting area 25 and a coagulation zone of the electrode parts 22, 23 is hardly disrupted. At the same time other areas of the guide gap 24 are easily accessible and thus also easy to clean. If the guide gap 24 has to be re-worked, for example, a coating has to be applied, this can then be carried out easily because of the improved access.

Figure 2:
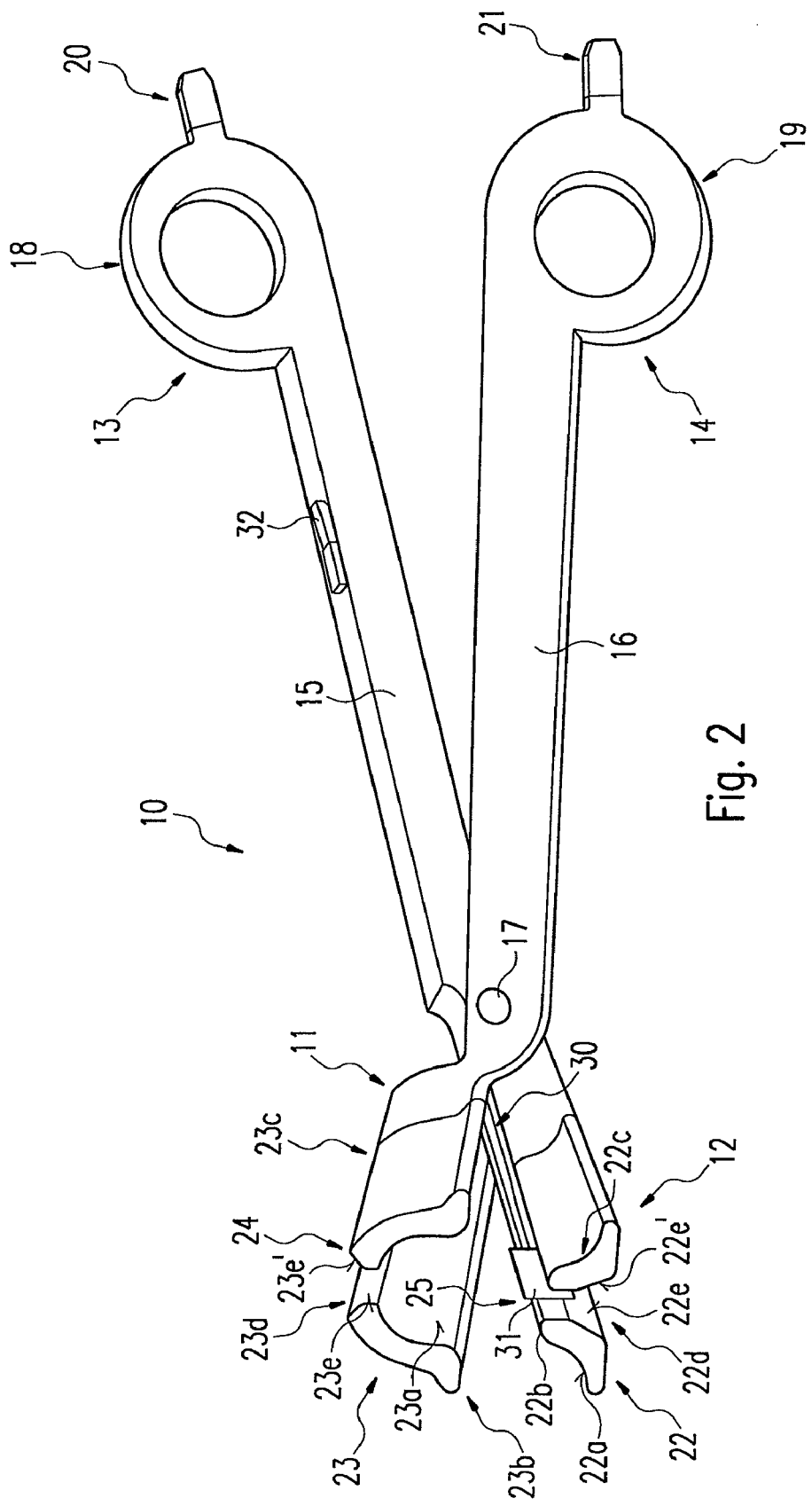
FIG. 2 is a perspective view of second embodiment of electrosurgical instrument.
Figure 3:
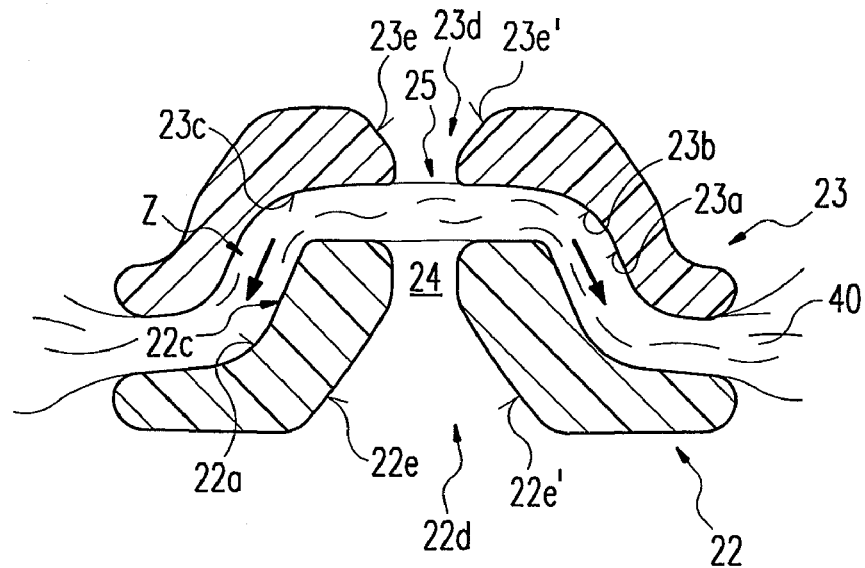
FIG. 3 is a schematic cross-sectional view from the front of the electrode arrangement of the second embodiment shown in FIG. 2.

FIG. 2 shows a perspective drawing of an electrosurgical instrument with an electrode layout according to the invention in a second preferred embodiment. FIG. 3 shows the schematic front view section of the electrode layout according to the second preferred embodiment from FIG. 2. The instrument 10 is constructed for procedures on the open body cavity. Two limbs of the electrosurgical instrument 10 are identified in the figure by reference numbers 15 and 16. The two limbs 15, 16 are connected to each other via a spindle 17 and can swivel around the same. They comprise electrode parts 22, 23 fitted with distal ends 11, 12 wherein the electrode parts 22, 23 are positioned opposite each other. A vessel or tissue 40 can, for example, be gripped, and be coagulated by means of a HF current being passed through it, with the aid of the electrode parts 22, 23 which comprise coagulation surfaces 22a, 23a. Moreover, handles 18, 19 are provided which connect to the respective proximal ends 13, 14 of the limbs 15, 16. The proximal ends 13, 14 of the limbs 15, 16 each end in a current connection element or a current supply device 20, 21 for the connection of the electrosurgical instrument 10 to a HF generator (not depicted) which generates HF voltage, so that the HF current can, for example, be passed through the electric cables (not shown) running through the instrument 10 to the electrode parts 22, 23.

The electrode layout corresponds largely to that described in FIG. 1. The electrode parts 22, 23 comprise also in this embodiment two respective areas where respective separation surfaces 22e, 22e', 23e, 23e' positioned opposite each other tapering in the direction of the coagulation surface are provided. The guide gap 24 thus expands here also in the direction facing away from cutting area 25 between the electrode parts 22, 23 at each electrode part 22, 23. Due to the guide gap 24 the tissue 40 can be cut by means of a cutting instrument 30, while still being held by the electrode parts 22, 23.

The electrode parts 22, 23 are, however, constructed in such a way that one electrode part 23 covers the other electrode part 22 when the limbs 15, 16 are bought together. As can be seen from the figure the electrode parts 22, 23 comprise a curvature. One electrode part 22 has a convex curvature 22b and electrode part 23 positioned opposite the concave electrode part has a concave curvature 23b. The electrode parts 22 thus fit essentially positively together when the limbs 15, 16 are brought together. As a result of the curved electrode parts 22, 23 the tissue 40 is pulled in the direction of the end areas of electrode parts 22, 23, that is to say it is stretched in a direction of pull Z. The electrode parts 22, 23 thus form tensioning areas 22c, 23c. The tissue 40 is then easier to cut, as tissue fibres are aligned at right angles to a cutting direction and the tissue 40 becomes thinner in the procedure. Because of the tight fit the tissue 40 is fixed in a tensioned state between the limbs 15, 16. The electrode parts 22, 23 in this embodiment are essentially formed completely as tensioning areas 22c, 23c. Alternatively, it is possible that only sections of the electrode parts form tensioning areas.

The cutting instrument 30 comprises a blade 31 on a shaft and is housed during a coagulation phase within the limb 15. For the cutting procedure the cutting instrument 30 can be positioned on the already coagulated tissue and for cutting tissues 40 it can be moved at a defined feed rate. This occurs in this embodiment, for example, by means of a control unit (not shown) which controls the cutting instrument 30 and is activated by a finger switch 32. As the cutting instrument 30 is integrated in the electrosurgical instrument 10 a change of instruments and thus disruption of an operation procedure is avoidable.

Alternatively, it possible for the user to actuate the cutting instrument 30 mechanically. The surgeon can then push the blade 31 when required through the limb 15 to and through the tissue. If no device for cutting the tissue is provided on the electrosurgical instrument the guide gap has then to be constructed in such a way that a cutting instrument being introduced from the outside, for example surgical scissors, can be placed with sufficient accuracy on the pretensioned tissue.

For a practical application a spacer (not shown) or similar device maintaining a gap between the electrode parts 22, 23 is constructed on the electrosurgical instrument 10, so that direct contact, and thus a short circuit, between the coagulation surfaces 22a, 23a of the electrode parts 22, 23 can be prevented. The spacer can, for example, be formed at one of the limbs 15, 16.

Alternatively, it is possible to construct the spacer as an insulating section on the electrode parts. Due to the heat conducting properties of the insulating section coagulation is also guaranteed at the same.

The electrosurgical instrument 10 shown in FIG. 2, as already mentioned, is constructed for use on the opened body cavity. The principle of the electrode parts having tapering separation surfaces can also be employed in endoscopy. The electrode parts attached to the limbs, and if required the cutting instrument, are then, for example, operated via a handle attached to a shaft or a control unit is provided so that actuation of the electrode parts and/or the cutting instrument is controlled by it.

Figure 5:
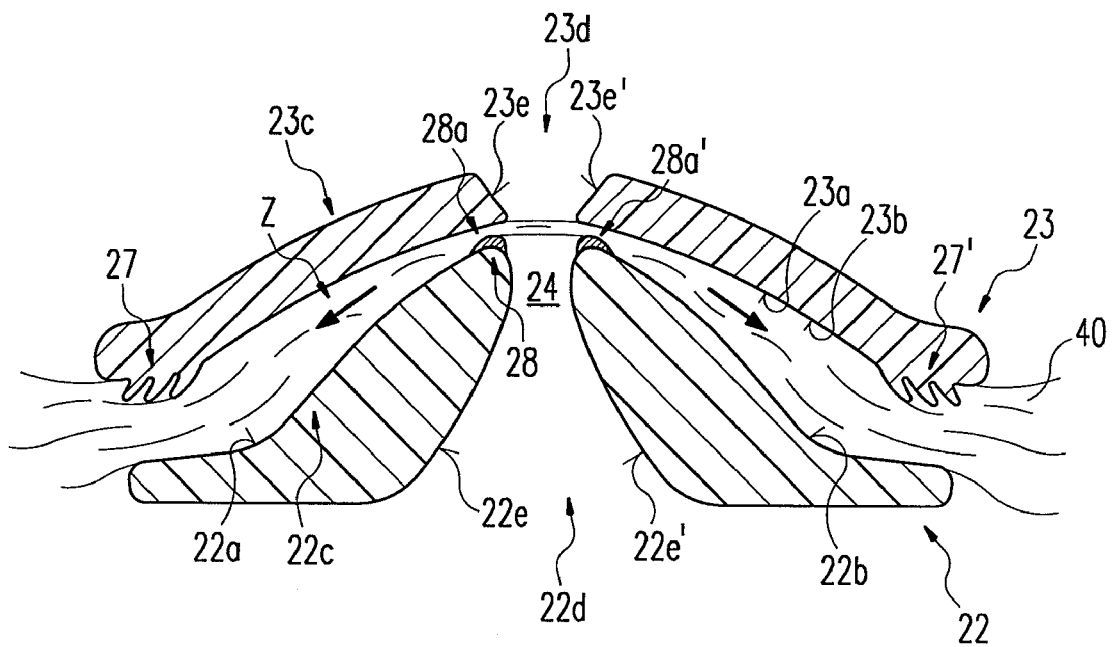
FIG. 5 is a schematic cross-sectional view from the front of a fourth embodiment of the electrode arrangement.
Figure 4:
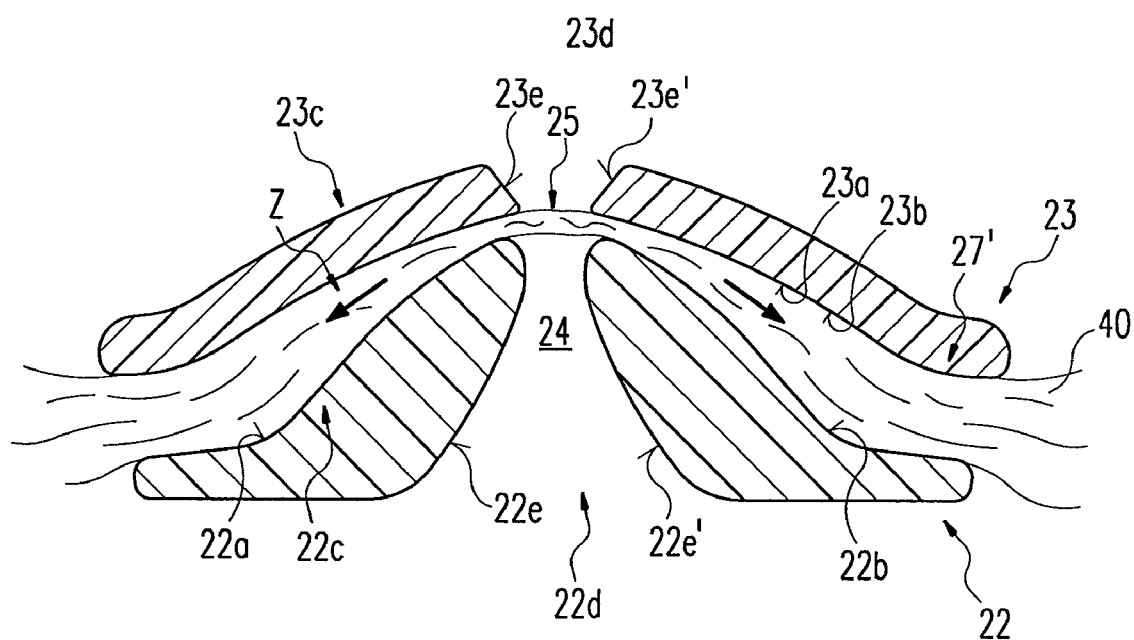
FIG. 4 is a schematic cross-sectional view from the front of a third embodiment of electrode arrangement.

FIGS. 4 and 5 respectively show an enlarged front view section of an electrode layout in a third and fourth embodiment. The electrode parts 22, 23 correspond essentially to the embodiment of that shown in FIGS. 2 and 3. Moreover electrode parts 22, 23 comprise also two respective areas, where separation surfaces 22e, 22e', 23e, 23e' arranged opposite each other tapering in the direction of the coagulation surface 22a, 23a are provided. The guide gap 24 thus also expands here in the direction facing away from a cutting area 25 between the electrode parts 22, 23 at each electrode part 22, 23.

In this embodiment the electrode part 22 has a convex curvature in a first central section while the electrode part 23 positioned opposite has a concave curvature in a second central section. A radius of curvature of the concave coagulation surface 23a is greater than a radius of curvature of the convex coagulation surface 22a. The curvatures 22b, 23b run along longitudinal axes of the distal ends 11, 12 in such a way that a vessel or tissue 40 that is held between the distal ends 11, 12 and extends perpendicularly to the longitudinal axes is held with a pressure that increases towards the first and second central sections. Due to the curvatures 22b, 23b the electrode parts 22, 23 in these embodiments are also formed as tensioning areas 22c, 23c. As a result of the tensioning areas 22c, 23c the tissue 40 is stretched in a direction of pull Z towards the end regions of the electrode parts 22, 23. The fibres of the tissue 40 are thus aligned at right angles to a cutting direction, so that the tissue 40 is easier to cut.

FIG. 5 differs essentially from the electrode layout shown in FIG. 4 only in that a protruding insulating section 28, formed from two part sections 28a, 28a', is provided directly adjacent to an open region 22d at the convex electrode part 22 which is divided by the open region 22d into two areas. The part sections 28a, 28a' of the insulating section 28 extend preferably parallel to a crest of the electrode part 22. Thus a short circuit between the electrode parts 22, 23 is prevented when they are brought together. The part sections 28a, 28a' of the insulating section 28 support the tensioning effect of the tensioning area 22 on the one hand and facilitate bending of the clamped tissue 40 on the other. A reliable hold of the same between the electrode parts 22, 23 is thus ensured.

Alternatively, it would be possible to construct the insulating section at the coagulation surface 22a in such a way that it also extends continuously along the crest of the coagulation surface 22a, but is essentially flush with it. The insulating section is then fitted into the coagulation surface 22a. This is possible because the insulating section would be provided at the first central section of the coagulation surface 22a and would thus reach the opposite coagulation surface 23a first and exclusively when the limbs 15, 16 are brought together. It would be advantageous if the insulating section in this embodiment is protected by being housed in the respective electrode part 22 and is thus safe from wear.

The insulating section 28 is preferably constructed from ceramic or diamond. Both materials show amongst other things a high corrosion resistance and high wear resistance to mechanical stress.

The electrode part 23 having a concave curvature 23b comprises a saw tooth profile 27, 27' at the end areas. The teeth can, for example, be arranged in such a way that during the bringing together of the limbs they continue to grip the tissue 40 and transport it in the direction of pull Z. This increases the tension in the tissue 40 considerably. Care must, however, be taken that injury to the tissue 40 caused by the profile is avoided, so the teeth are preferably constructed as nodules.

The nodules are preferably laid out in such a way that the tissue 40 is held by the profile 27, 27' in its tensioned position when the limbs are opened slightly. The profile 27, 27' acts therefore as an arrangement of barbs.

Alternatively or in addition it would be possible to construct the surface profile supporting the tensioning effect in such a way that in particular between the electrode parts having the same radius of curvature at least one constriction is provided. This means that the coagulation surfaces of the electrode parts are preferably constructed at both end areas in such a way that the tissue during the bringing together of the limbs is transported in the direction of the end areas and is clamped in a constriction opposite the remaining area when the limbs have been brought together. This constriction has the additional advantage that the coagulation surfaces can essentially have a smooth design and are thus easy to clean. Because of the smooth surface injury to the tissue is also avoided.

An insulating section arranged between the electrode surfaces can advantageously be constructed as a surface profile supporting a tensioning effect of the tensioning areas. A short circuit is thus prevented from occurring between the electrode parts in the simplest way as well as the tensioning of the tissue being increased.

LIST OF REFERENCE NUMERALS

10 Electrosurgical instrument
11 Distal end
12 Distal end
13 Proximal end
14 Proximal end
15 Limb
16 Limb
17 Spindle
18 Handle
19 Handle
20 Current connection element, current supply device
21 Current connection element, current supply device
22 Electrode part
22a Coagulation surface
22b Convex curvature
22c Tensioning area
22d Open region
22e, 22e' Separation surface
23 Electrode part
23a Coagulation surface
23b Concave curvature
23c Tensioning area
23d Open region
23e, 23e' Separation surface
24 Guide gap
25 Cutting area
27, 27' Profile
28 Insulating section
28a, 28a' Part section of the insulating section
30 Cutting instrument
31 Blade
32 Finger switch
40 Tissue, vessel
Z Direction of pull

The invention claimed is:

1. An electrosurgical instrument including:
   two articulated limbs which can be actuated in the manner of a cutting or clamping tool,
   electrode parts with coagulation surfaces positioned opposite each other at distal ends of the limbs for gripping tissue and adapted to pass a coagulating current through said tissue to cause its coagulation, at least one electrode part defining one open region adapted as a guide gap for a cutting instrument whereby said one electrode part is divided into at least two areas and said cutting instrument can be applied to clamped tissue for a cutting procedure, and
   current supply devices for supplying the coagulation current to said electrode parts from a HF generator, and wherein
   said at least two areas of said at least one electrode part define respective separation surfaces that are arranged opposite each other and that taper in the direction of said coagulation surfaces such that a width of said guide gap increases substantially continuously from a portion of said guide gap substantially adjacent to said clamped tissue to a portion of said guide gap most distal from said clamped tissue.

2. The electrosurgical instrument according to claim 1, wherein said opposite electrode parts both define said open regions that substantially align with one another when said limbs are brought together.

3. The electrosurgical instrument according to claim 1 including a cutting instrument that is constructed as an integral part of the electrosurgical instrument.

4. The electrosurgical instrument according to claim 3, wherein said cutting instrument is adapted to be actuated by at least one of a mechanical or an electrical means.

5. The electrosurgical instrument according to claim 3, comprising a control unit and wherein said cutting instrument is adapted for cutting by means of a HF current and is connected to said control unit, which controls supply of the cutting current depending on the operation phase.

6. The electrosurgical instrument according to claim 1, wherein the electrode parts each comprise at least one tensioning area adapted to tension tissue clamped between the electrode parts such that said tissue is pretensioned prior to a cutting procedure being carried out on the pretensioned tissue by the cutting instrument.

7. The electrosurgical instrument according to claim 6, wherein one of said tensioning areas defines a convex curvature in at least a first central section and an opposite said tensioning area comprises a concave curvature in at least a second central section such that when the limbs are brought together these tensioning areas fit together.

8. The electrosurgical instrument according to claim 6, wherein one of said tensioning areas defines at least a convex curvature in a first central section and an opposite said tensioning area defines a concave curvature in at least a second central section, the radius of curvature of the concave tensioning area being greater at least in the second central section than the radius of curvature of the convex tensioning area in the first central section and wherein said curvatures run along longitudinal axes of said distal ends in such a way that tissue clamped between the distal ends extends perpendicularly to said longitudinal axes and is retained by a pressure that increases in directions towards the first and second central sections.

9. The electrosurgical instrument according to claim 6, wherein at least one of a tensioning area and its opposing tensioning area defines a surface profile that produces the tensioning effect is constructed on the one tensioning areas and/or on the opposite tensioning area.

10. The electrosurgical instrument according to claim 9, wherein said surface profile is a saw tooth profile.

11. The electrosurgical instrument according to claim 9, wherein said surface profile is configured in such a way that at least one constriction is provided between the electrode parts.

12. The electrosurgical instrument according to claim 1, wherein an insulating section is provided on at least one coagulating surface that prevents direct electrical contact between the coagulating surfaces.

13. The electrosurgical instrument according to claim 12, wherein said insulating section comprises several segments.

14. The electrosurgical instrument according to claim 12, wherein said insulating section is structurally formed.

15. The electrosurgical instrument according to claim 12, wherein said insulating section is constructed from ceramic or from diamond.

16. The electrosurgical instrument according to claim 12, wherein said insulating section is configured as a surface profile that aids said tensioning effect.

17. The electrosurgical instrument according to claim 1 that is constructed as a laparoscopic instrument.

18. An electrosurgical instrument including:
two articulated limbs which can be actuated in the manner of a cutting or clamping tool,
electrode parts with coagulation surfaces positioned opposite each other at distal ends of the limbs for gripping tissue and adapted to pass a coagulating current through said tissue to cause its coagulation, at least one electrode part defining one open region adapted as a guide gap for a cutting instrument whereby said one electrode part is divided into at least two areas and said cutting instrument can be applied to clamped tissue for a cutting procedure, and
current supply devices for supplying the coagulation current to said electrode parts from a HF generator, and wherein
said at least two areas of said at least one electrode part define respective separation surfaces that are arranged opposite each other and that taper in the direction of said coagulation surfaces such that said guide gap comprises a generally V-shaped portion, said V-shaped portion of said guide gap being narrowest at a location substantially adjacent to said clamped tissue.

* * * * *